United States Patent
Holmes et al.

(10) Patent No.: US 9,791,420 B2
(45) Date of Patent: Oct. 17, 2017

(54) FLUIDLESS ROLLER PROBE DEVICE

(71) Applicant: The Boeing Company, Chicago, IL (US)

(72) Inventors: Tyler M. Holmes, Seattle, WA (US); Jeffrey R. Kollgaard, Seattle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 191 days.

(21) Appl. No.: 14/473,041

(22) Filed: Aug. 29, 2014

(65) Prior Publication Data

US 2016/0061785 A1    Mar. 3, 2016

(51) Int. Cl.
*G01N 29/04* (2006.01)
*G01N 29/22* (2006.01)
*G01N 29/24* (2006.01)
*G01N 29/265* (2006.01)
*G01N 27/90* (2006.01)

(52) U.S. Cl.
CPC ....... *G01N 29/2493* (2013.01); *G01N 27/902* (2013.01); *G01N 29/225* (2013.01); *G01N 29/24* (2013.01); *G01N 29/265* (2013.01); *G01N 2291/0258* (2013.01); *G01N 2291/106* (2013.01); *G01N 2291/2694* (2013.01)

(58) Field of Classification Search
CPC .... G01N 29/265; G01N 29/04; G01N 29/225; G01N 29/22; G01N 29/28; G01N 29/2493; G01N 2291/101; G01N 2291/2638; G01N 2291/2694; G01N 29/24

USPC ................ 73/635, 639, 633–634, 644, 865.5
See application file for complete search history.

(56) References Cited

U.S. PATENT DOCUMENTS

| | | | | |
|---|---|---|---|---|
| 3,257,843 A | * | 6/1966 | Cowan | G01N 29/2493 310/336 |
| 3,384,767 A | * | 5/1968 | Arnold | B06B 1/0622 257/416 |
| 3,541,840 A | * | 11/1970 | Phelan | G01N 29/2493 73/639 |

(Continued)

OTHER PUBLICATIONS

Ultrasonic Sensors Brochure, Sonatest, 2010.

*Primary Examiner* — Helen Kwok
(74) *Attorney, Agent, or Firm* — Economou Silfin LLP; John S. Economou

(57) ABSTRACT

A fluidless roller probe device for performing structural integrity testing. A drum sensor has a shaft, a barrel-shaped inner portion mounted on the shaft, a sensor array having transmit elements and receive elements positioned on an outer surface of the inner portion, and an outer portion positioned over the sensor array. A shaft encoder is coupled to the shaft of the drum sensor. A support structure is coupled to the shaft of the drum sensor. Processing circuitry coupled to the transmit elements and receive elements is configured to activate, based on a signal from the shaft encoder, only that transmit element closest to the surface of the part under test and to calculate an output signal based on signals received from the receive elements. The transmit and receive elements are either ultrasonic transducers or eddy current coils. The transmit and receive elements are arranged in a lattice-like configuration.

15 Claims, 5 Drawing Sheets

(56) References Cited

U.S. PATENT DOCUMENTS

| | | | | |
|---|---|---|---|---|
| 3,612,920 | A * | 10/1971 | Bantz | G10K 11/004 310/336 |
| 3,698,051 | A * | 10/1972 | Miller | B41J 2/1623 29/25.35 |
| 3,714,816 | A * | 2/1973 | Miller | B06B 1/0655 73/639 |
| 3,714,817 | A * | 2/1973 | Miller | B06B 1/0622 73/639 |
| 3,745,813 | A * | 7/1973 | Uozumi | G01N 29/28 73/624 |
| 3,771,354 | A * | 11/1973 | Miller | G01N 29/2437 73/625 |
| 4,102,204 | A * | 7/1978 | Kretz | A61B 8/4281 73/626 |
| 4,459,853 | A * | 7/1984 | Miwa | G01S 7/52079 73/626 |
| 4,472,974 | A | 9/1984 | Dickson et al. | |
| 4,523,122 | A * | 6/1985 | Tone | G10K 11/02 310/327 |
| 4,567,895 | A * | 2/1986 | Putzke | G10K 11/355 600/445 |
| 4,856,334 | A * | 8/1989 | Shearer | G01N 29/11 73/588 |
| 4,917,373 | A * | 4/1990 | Bourne | A63J 17/00 472/61 |
| 6,378,376 | B1 * | 4/2002 | Derman | G10K 11/352 600/446 |
| 6,536,553 | B1 * | 3/2003 | Scanlon | G01N 29/069 181/108 |
| 6,688,178 | B1 * | 2/2004 | Schmidt | G01N 29/2493 73/639 |
| 6,914,427 | B2 | 7/2005 | Gifford et al. | |
| 7,360,427 | B2 * | 4/2008 | Drinkwater | G01N 29/223 73/635 |
| 7,617,730 | B2 | 11/2009 | Georgeson | |
| 7,712,369 | B2 | 5/2010 | Georgeson | |
| 8,453,928 | B2 | 6/2013 | Melandso et al. | |
| 8,662,395 | B2 | 3/2014 | Melandso et al. | |
| 8,739,631 | B2 * | 6/2014 | Havira | G01N 29/2493 73/632 |
| 8,997,590 | B2 * | 4/2015 | Oberdoerfer | G01N 29/2493 310/326 |
| 9,010,187 | B2 * | 4/2015 | Bond-Thorley | G01N 29/04 73/639 |
| 2006/0053891 | A1 * | 3/2006 | Georgeson | G01N 29/221 73/624 |
| 2008/0309200 | A1 | 12/2008 | Melandso et al. | |
| 2011/0102263 | A1 * | 5/2011 | Angeletti | H01Q 3/40 342/373 |
| 2011/0115748 | A1 * | 5/2011 | Xu | G06F 3/0421 345/175 |
| 2012/0291555 | A1 * | 11/2012 | Hackenberger | G01N 29/2493 73/635 |
| 2012/0310093 | A1 * | 12/2012 | Tanabe | G01S 7/52049 600/443 |
| 2014/0150557 | A1 * | 6/2014 | De Miguel Giraldo | G01N 29/2493 73/635 |
| 2015/0242015 | A1 * | 8/2015 | Cho | G06F 3/044 345/174 |

* cited by examiner

FLUIDLESS ROLLER PROBE DEVICE

FIELD

This disclosure relates generally to a roller probe device for hand scanning, and more particularly to a roller probe device that operates without fluid.

BACKGROUND

Structural integrity testing is used in the aircraft industry to validate the health of aircraft structures. One way to perform such testing is by scanning an ultrasonic array over a surface of the structure under test. Another way to perform such testing is by use of eddy current array probes. Ultrasonic roller probes have been used to perform ultrasonic scanning. However, conventional ultrasonic roller probes include a fluid-filled drum with an ultrasonic array in the center of the drum. As the outer surface of the drum moves across the surface of the structure under test, sound from the array is coupled through the fluid and the outer surface and into such structure. These conventional ultrasonic roller probes have a number of drawbacks, including, inter alia, the need to fill (and refill) the drum, the possibility that air bubbles or pockets within the fluid could distort the test results, limitations on the scanning speed, limitations on scanning resolution and the possibility that uneven pressure applied to the roller probe during test could distort the test results (for example, due to uneven test surfaces). Eddy current array probes have been used to perform eddy current scanning. However, conventional eddy current arrays include a block or support structure behind the array. The array is bonded or attached to the support block and scanned by sliding the array across surfaces. These conventional eddy current arrays have a number of drawbacks including the friction and wear on the sensor surface, limitations on scanning speed, and the ability to scan rough surfaces.

Accordingly, there is a need for a device which overcomes the drawbacks of the conventional devices described above.

SUMMARY

In one aspect, a device for performing structural integrity testing is disclosed. The device includes a drum sensor, a support structure and processing circuitry. The drum sensor has a shaft, a barrel-shaped inner portion mounted on the shaft, a sensor array having a plurality of transmit elements and a plurality of receive elements and positioned on an outer surface of the inner portion, and an outer portion positioned over the sensor array. The support structure is coupled to the shaft of the drum sensor. The processing circuitry is coupled to the transmit elements and receive elements and is configured to activate at least one of the transmit elements and to calculate an output signal based on signals received from the receive elements.

In a further embodiment, the device includes a shaft encoder coupled to the shaft of the drum sensor, the drum sensor rotates as a user moves the device using the support structure across a surface of a part under test, the processing circuitry is also coupled to receive a signal from the shaft encoder, the transmit elements are arranged in the sensor array such that only one of the plurality of transmit elements is closest to the surface of the part under test at any point in time, and the processing circuitry is configured to activate, based on a signal from the shaft encoder, only that transmit element closest to the surface of the part under test.

In one still further embodiment, each of the plurality of transmit elements is an ultrasonic transducer configured to output an acoustic signal upon activation and each of the plurality of receive elements is an ultrasonic transducer configured to receive an acoustic signal. The plurality of transmit elements and the plurality of receive elements are preferably arranged in a lattice-like configuration.

In another still further embodiment, each of the plurality of transmit elements and receive elements is an eddy current coil. The plurality of transmit elements and the plurality of receive elements are preferably arranged in a lattice-like configuration.

The processing circuitry may be positioned within the inner portion of the drum sensor. The outer portion of the drum sensor may be an acoustic material or may be a thin protective membrane. The support structure may include a handle. The device may further include a stabilizing wheel coupled to the support structure.

In another aspect, a drum sensor for a device for performing structural integrity testing is disclosed. The drum sensor includes a shaft, a barrel-shaped inner portion mounted on the shaft, a sensor array having a plurality of transmit elements and a plurality of receive elements and positioned on an outer surface of the inner portion, and an outer portion positioned over the sensor array. In one further embodiment, each of the plurality of transmit elements is an ultrasonic transducer configured to output an acoustic signal upon activation and each of the plurality of receive elements is an ultrasonic transducer configured to receive an acoustic signal. The plurality of transmit elements and the plurality of receive elements may preferably be arranged in a lattice-like configuration. In another further embodiment, each of the plurality of transmit elements and receive elements is an eddy current coil. The plurality of transmit elements and the plurality of receive elements are preferably arranged in a lattice-like configuration.

In still another aspect, a method for performing structural integrity testing is disclosed. An input signal is received from a shaft encoder coupled to a drum sensor, the input signal providing an indication of a position of the drum sensor with respect to a surface of a part under test. A transmit element closest to the surface of the part under test is identified, based on the input signal from the shaft encoder. The identified transmit element is activated. An input signal is received from a plurality of receive elements. Finally, an output signal is calculated based on receive input signal from the plurality of receive elements.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure.

Figure 1:
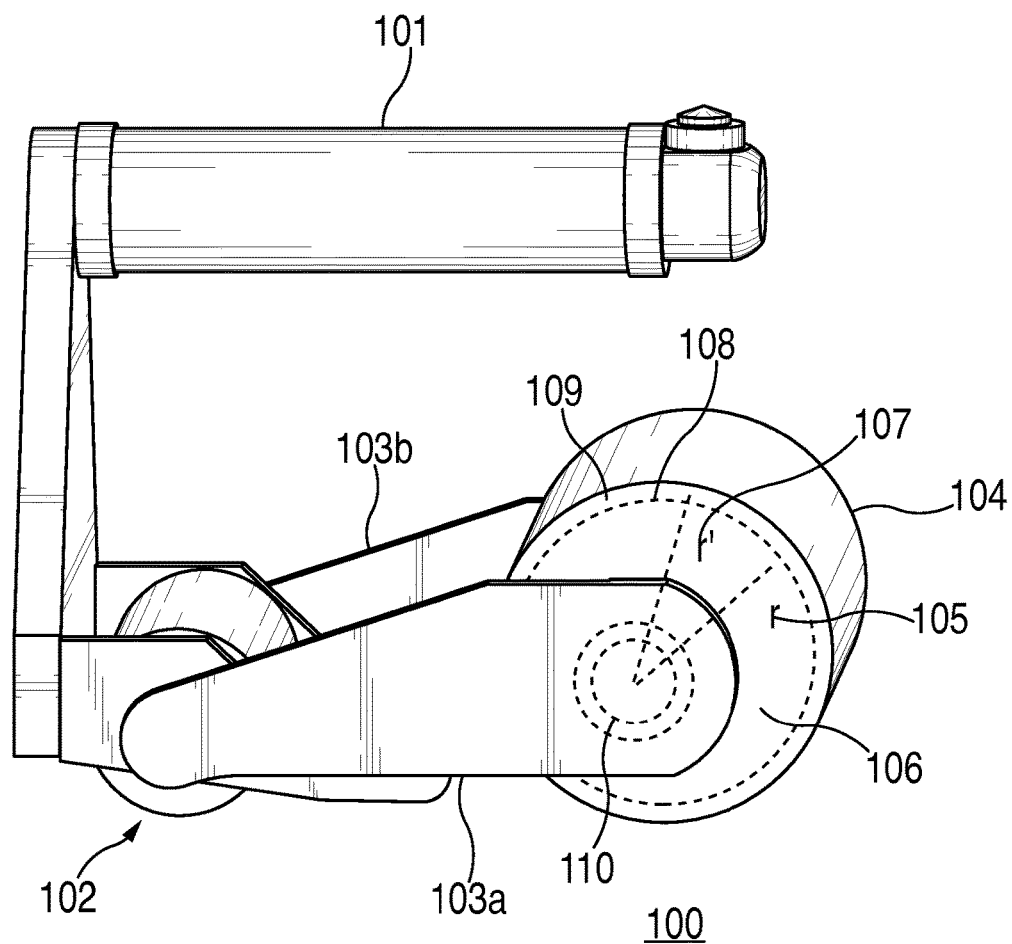
FIG. 1 is a diagram of a roller probe device according to a first embodiment of the present disclosure.

Referring now to FIG. 1, a roller probe device 100 according to a first embodiment of the present disclosure includes a sensing drum 104 coupled to brackets 103a, 103b, a stabilizing wheel 102 and a handle assembly 101. A connector (not shown) is provided on handle assembly 101 for providing an output signal, preferably via a conventional interface such as a USB connector. Stabilizing wheel 102 ensures that sensing drum 104 contacts a surface of the part under test evenly while a user holding handle 101 moves roller probe device 100 across such surface. As one of ordinary skill in the art will readily recognize, other structures may be used for the same purpose instead of stabilizing wheel 102 and, in some cases, stabilizing wheel 102 may be omitted. Roller probe device 100 provides for rapid inspection of large areas by creating a two-dimensional scan in the rolling direction of probe 100.

Sensing drum 104 has a radius r' 107 and includes an inner barrel shaped support structure 106 (having a radius r 105) mounted on a shaft 110, a sensor array portion 108 over the support structure 106, and an outer portion 109 comprising an acoustic material that acts as a delay line and protects the array and allows for good acoustical coupling with the surface of the part under test so that sound is passed into the part under test in a known controlled manner. One example of such acoustic material is a silicone rubber. One of ordinary skill in the art will readily recognize that other types of materials may also be used, including but not limited to a natural rubber material. Processing circuitry (shown and discussed with respect to FIG. 3 below) can be housed within support structure 106 or within handle assembly 101. A shaft encoder (not shown) is mounted on the shaft 110 to keep track of the rotational position of drum 104.

By eliminating the need for a fluid filled drum for inspection, roller probe device 100 provides for easier inspection from odd angles since there is no danger of bubbles forming between an internal sensor array and an outer surface of the drum, which would negatively affect any collected data. Roller probe device 100 also eliminates any need to fill and refill the drum with fluid as required by conventional devices. Further, by replacing the conventional fluid-filled drum with a solid drum, scans are less likely to be distorted by pressure differences on a surface of drum 104. Conventional drums can deform along the external surface thereof due to uneven surfaces (ramps, holes, etc.) on the part under test.

Figure 2:
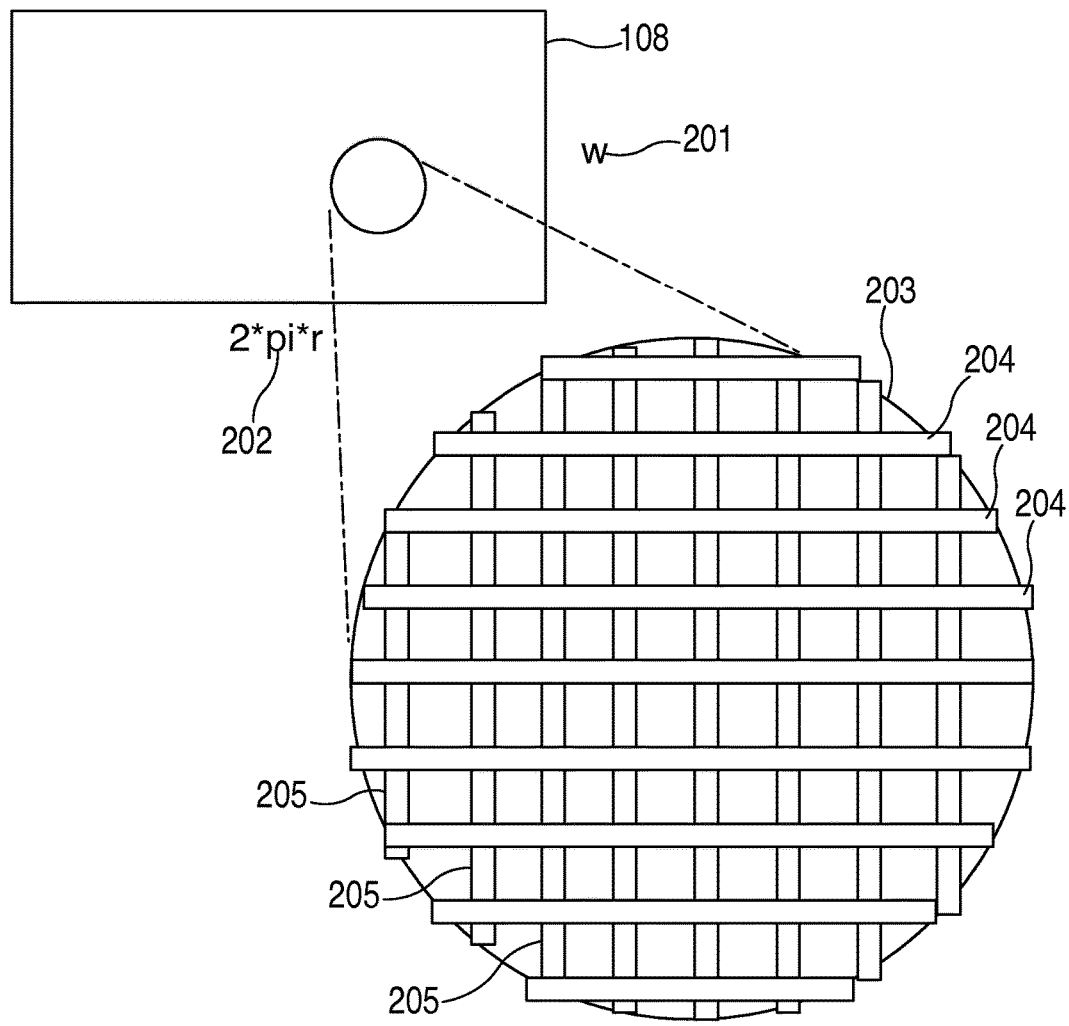
FIG. 2 is a diagram of an embodiment of a transducer array for the roller probe device of FIG. 1.

Referring now to FIG. 2, ultrasonic sensor array 108 can be formed or fabricated into a cylinder and has a width w 201 and a length $2*\pi*r$ 202 where r corresponds to the radius of support structure 106 shown in FIG. 1. A portion 203 of sensor array 108 is shown magnified in FIG. 2 to show the composition thereof in more detail. In particular, sensor array 108 consists of a plurality of parallel receive elements 204 shown horizontal in FIG. 2 and a plurality of parallel transmit elements 205 shown vertical in FIG. 2. As evident, the receive elements 204 and the transmit elements 205 are positioned in a lattice-like configuration, with the receive elements 204 perpendicular to the transmit elements 205. When sensor array 108 is positioned on support structure 106, the parallel receive elements 204 each run around the entire circumference of support structure 106 while the transmit elements 205 are perpendicular to the receive elements 204 and are distributed evenly around the circumference of support structure 106. Each receive element 204 is preferably an ultrasonic transducer that is configured to only sense acoustic signals. Each transmit element 205 is preferably an ultrasonic transducer that is configured to only output acoustic signals. In combination, transmit elements 205 and receive elements 204 operate to perform pulse-echo type inspection in a manner similar to that disclosed in U.S. Pat. No. 7,617,730 B2 issued on Nov. 17, 2009 (the '730 Patent"), incorporated by reference herein in its entirety, and U.S. Pat. No. 7,712,369 B2 issued on May 11, 2010 ("the '369 Patent"), also incorporated by reference herein in its entirety, although the arrays employed in the '730 and '369 Patents include individual elements instead of an array in a lattice-like configuration as in the present disclosure.

Sensor array 108 provides for faster scanning speeds because a single transmit element 205 is triggered at a time as such element comes into contact with a surface of the part under test. Roller probe device 100 provides for higher resolution scans due to the lattice-like configuration of the sensor array 108 (instead of individual elements). In addition, since the individual send-receive elements used in prior arrays are not needed, sensor array 108 is less expensive to fabricate than such prior arrays.

Figure 3:
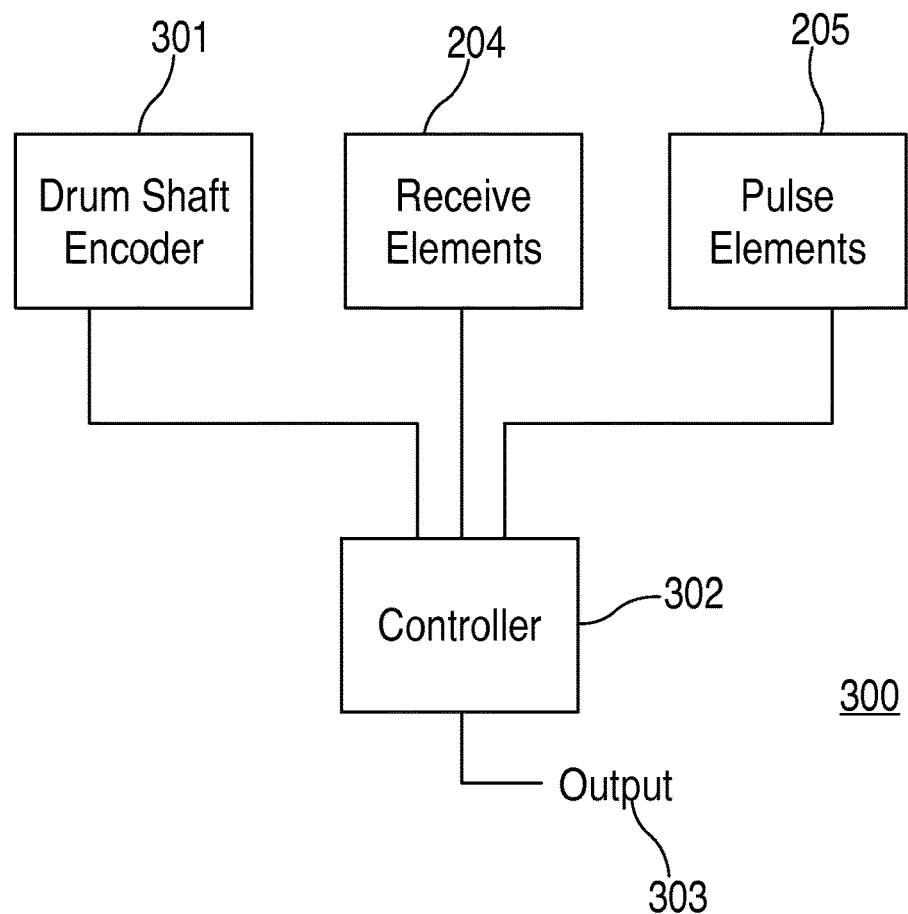
FIG. 3 is block diagram of a processing system for the roller probe device of FIG. 1.

Referring now to FIG. 3, the processing circuitry 300 for roller probe device 100 is shown in block diagram form. A controller 302 is separately coupled to transmit elements 205, receive elements 204 and to drum shaft encoder 301. As discussed above, drum shaft encoder 301 provides controller 304 with the ability to keep track of the rotational position of drum 104 and, in particular, to track which of the transmit elements 205 is closest to a surface of the part under test (through outer portion 109) at any point in time. In operation, as drum 104 rolls across the surface of the part under test and based on the signal from shaft encoder 301, controller 304 sequentially activates each of the transmit elements 205 as that element comes into contact (via outer portion 109) with the surface of the part under test. Receive elements 204 receive acoustic signals reflected by a back surface of the part under test, and controller 302 processes signals from the receive elements 204 to generate an output signal 303 in a manner similar to that disclosed in the '730 and '369 Patents. Roller probe device 100 also includes a controller 304 which performs all necessary processing, making possible to interface directly with a computer via a conventional interface, e.g., a USB interface, instead of requiring a specialized cable.

Figure 4:
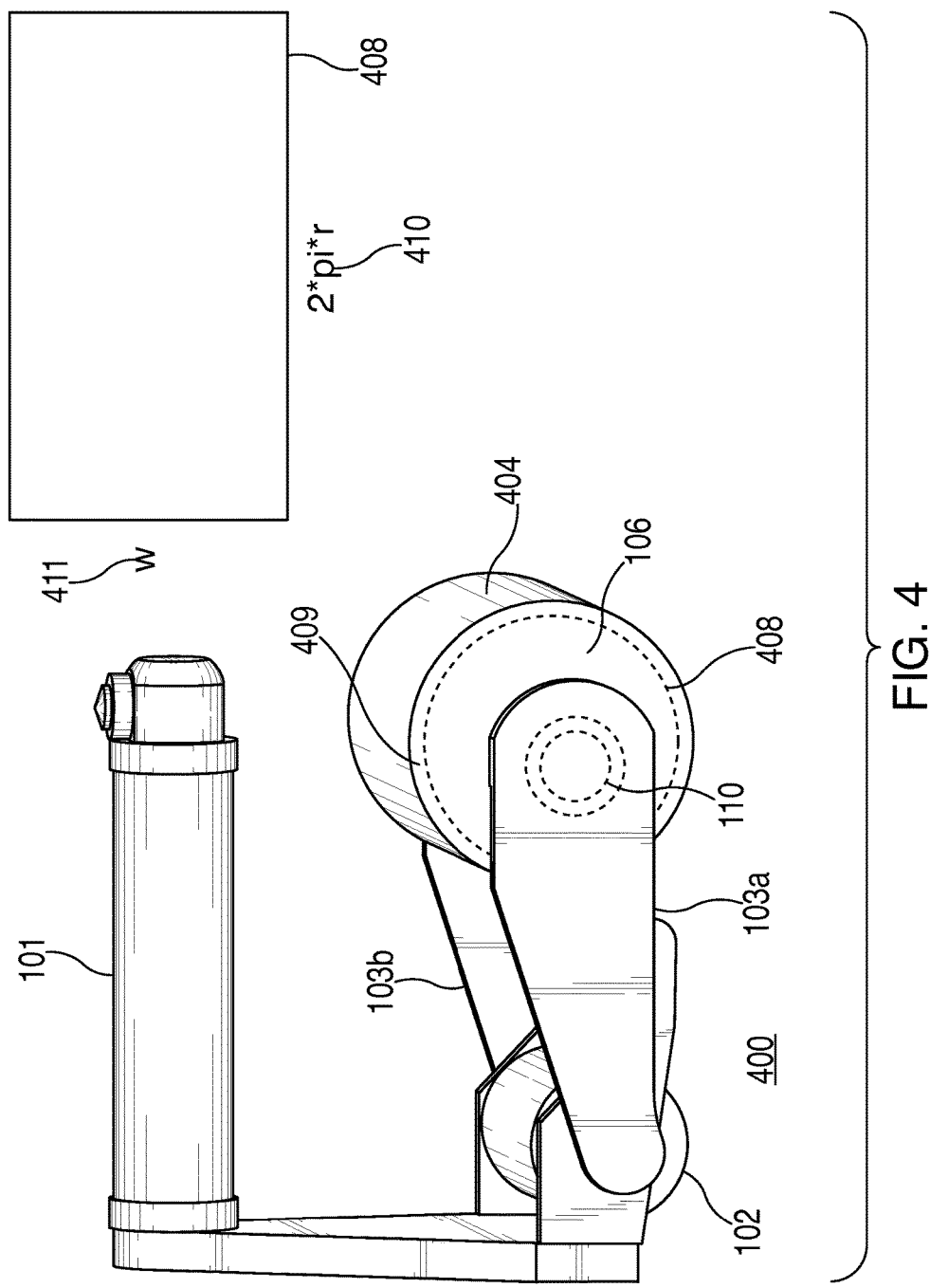
FIG. 4 is a diagram of a roller probe device according to a second embodiment of the present disclosure.

Referring now to FIG. 4, a roller probe device 400 according to a second embodiment of the present disclosure includes a sensing drum 404 which includes an eddy current sensor array 408 (instead of the ultrasonic sensor array 108 of the first embodiment). Sensor array 408 has a width w 411 and a length $2*\pi*r$ 410 where r corresponds to the radius of support structure 106 as with the first embodiment. The construction of eddy current sensor array 408 is described in U.S. Pat. No. 6,914,427 B2 that issued on Jul. 5, 2005 ("the '427 Patent"), incorporated by reference herein in its entirety. As described in the '427 Patent, eddy current sensor array 408 includes first coils and second coils, with the first coils arranged perpendicularly to the second coils. Thus, the eddy current sensor array 408 in roller probe device 400 includes first coils that circle the circumference of drum 404 and second coils that are perpendicular to the first coils (similarly to the elements of sensor array 108 of the first embodiment). In addition, sensing drum 404 includes an outer portion 409 comprising a thin protective material that acts as a wear face and protects the array 408 and allows for electromagnetic coupling with the surface of the part under test. One example of such protective material is a Kapton® film. One of ordinary skill in the art will readily recognize that other types of materials may also be used, including but not limited to a plastic or rubber film material. In operation, roller probe device 400 includes processing circuitry (e.g., a controller) which activates each second coil (by supplying a current to such coil) as such coil contacts a surface of the part under test (based on an input from shaft encoder positioned on shaft 110) and senses any current induced in the first coils to generate an output signal, in a manner similar to that of the first embodiment. Thus, the second embodiment provides similar advantages to the first embodiment over fluid-based sensing systems, while employing an alternative type of sensing (i.e., eddy current versus ultrasonic). In addition, by eliminating the need for an array in sliding contact with the part (as necessary with prior art eddy current probes), roller probe device 400 provides a faster and more durable inspection system, particularly for surfaces that are not smooth.

Figure 5:
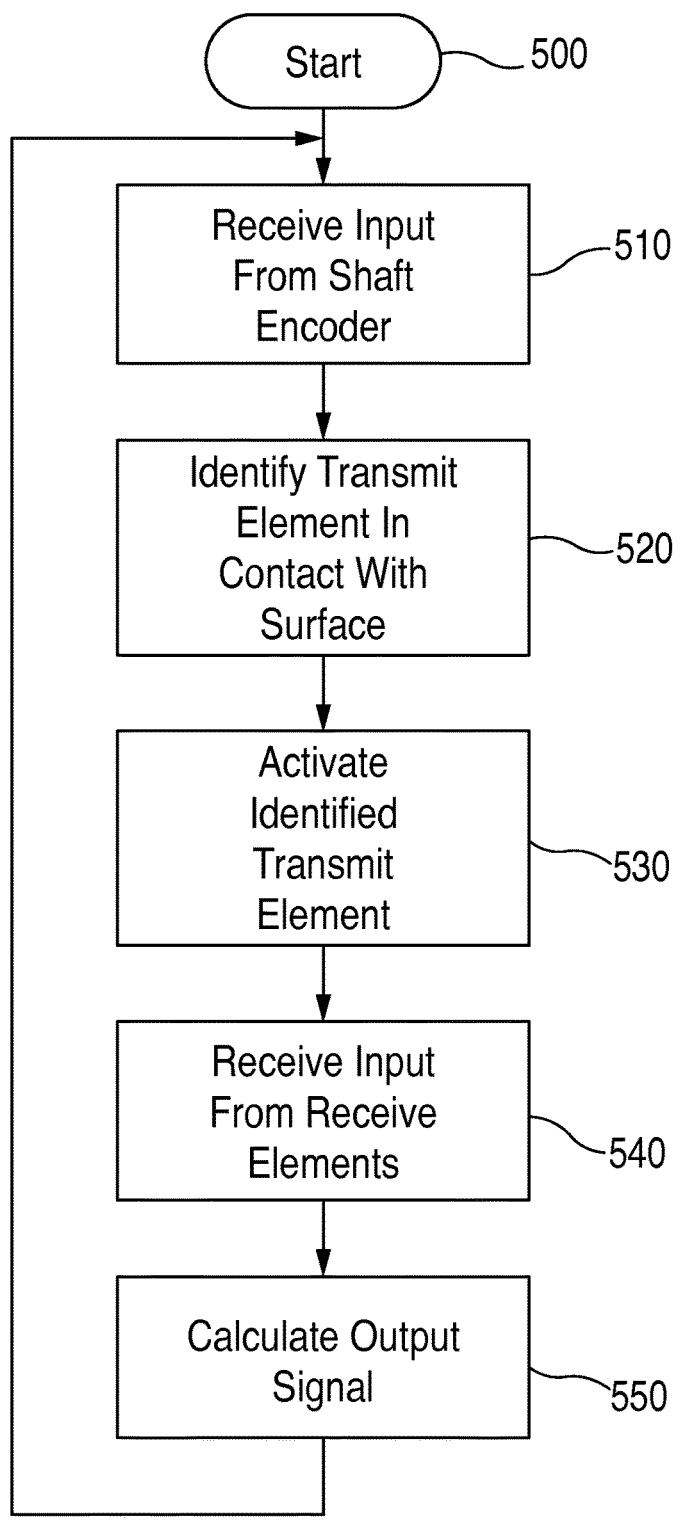
FIG. 5 is a flowchart of a method performed by the first and second embodiments of the present disclosure.

Referring now to FIG. 5, a flowchart is provided to show the steps performed by the controller 302 during testing of a part using the fluidless roller probe device of the present disclosure. In particular, as shown in FIG. 5, as the scan is started by a user moving the probe over the surface of a part under test (step 500), controller 302 receives input from the shaft encoder (step 510). Based on this input, controller 302 identifies the transmit element (transmit element) that is currently closest to the surface (step 520). Controller 302 then activates the identified transmit element (step 520). For the first embodiment, activation of the transmit element means causing the identified transmit element to output an acoustic signal. For the second embodiment, activation of the transmit element means causing a current to flow through the identified transmit element. Controller 302 then receives input from the receive elements (step 540) and calculates an output signal (and provides such signal on output line 303) (step 550). This process repeats for the duration of the scan as the fluidless roller probe device is moved across the surface of the part under test.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. A device for performing structural integrity testing, comprising:
    a drum sensor having a shaft, a barrel-shaped inner portion mounted on the shaft, a sensor array having a plurality of transmit elements and a plurality of receive elements, the transmit elements separate from the receive elements, the transmit elements positioned perpendicular to the receive elements, the sensor array positioned on an outer surface of the barrel-shaped inner portion, and an outer portion positioned over the sensor array;
    a support structure coupled to the shaft of the drum sensor;
    processing circuitry coupled to the transmit elements and the receive elements and configured to activate at least one of the transmit elements and to calculate an output signal based on signals received from the receive elements; and
    wherein the plurality of transmit elements are arranged in parallel to each other around a circumference of the outer surface of the barrel-shaped inner portion and the plurality of receive elements are arranged parallel to each other and perpendicular to the circumference of the outer surface of the barrel-shaped inner portion, each of the plurality of receive elements extending across the outer surface of the barrel-shaped inner portion.

2. The device of claim 1, further comprising a shaft encoder coupled to the shaft of the drum sensor, wherein the drum sensor rotates as a user moves the device using the support structure across a surface of a part under test, wherein the processing circuitry is also coupled to receive a signal from the shaft encoder, wherein the transmit elements are arranged in the sensor array such that only one of the plurality of transmit elements is closest to the surface of the part under test at any point in time, and wherein the processing circuitry is configured to activate, based on the signal from the shaft encoder, only that transmit element closest to the surface of the part under test.

3. The device of claim 2, wherein each of the plurality of transmit elements comprises an ultrasonic transducer configured to output an acoustic signal upon activation and wherein each of the plurality of receive elements comprises an ultrasonic transducer configured to receive a return acoustic signal reflected by a part under test.

4. The device of claim 2, wherein each of the plurality of transmit elements and receive elements comprises an eddy current coil.

5. The device of claim 2, wherein the processing circuitry is positioned within the barrel-shaped inner portion of the drum sensor.

6. The device of claim 3, wherein the outer portion of the drum sensor is an acoustic material.

7. The device of claim 2, wherein the support structure includes a handle.

8. The device of claim 2, further comprising a stabilizing wheel coupled to the support structure.

9. A drum sensor for a device for performing structural integrity testing, comprising:
    a shaft;
    a barrel-shaped inner portion mounted on the shaft;
    a sensor array having a plurality of transmit elements and a plurality of receive elements, the transmit elements separate from the receive elements, the transmit elements positioned perpendicular to the receive elements, the sensor array positioned on an outer surface of the barrel-shaped inner portion;
    an outer portion positioned over the sensor array; and
    wherein the plurality of transmit elements are arranged in parallel to each other around a circumference of the outer surface of the barrel-shaped inner portion and the plurality of receive elements are arranged parallel to each other and perpendicular to the circumference of the outer surface of the barrel-shaped inner portion, each of the plurality of receive elements extending across the outer surface of the barrel-shaped inner portion.

10. The drum sensor of claim 9, wherein each of the plurality of transmit elements comprises an ultrasonic transducer configured to output an acoustic signal upon activation and wherein each of the plurality of receive elements comprises an ultrasonic transducer configured to receive a return acoustic signal reflected by a part under test.

11. The drum sensor of claim 9, further comprising
processing circuitry positioned within the barrel-shaped inner portion of the drum sensor and coupled to the transmit elements and receive elements, the processing circuitry configured to selectively activate only one of the plurality of transmit elements and to calculate an output signal based on signals received from the receive elements;
a shaft encoder coupled to the shaft; and
wherein the processing circuitry is also coupled to receive a signal from the shaft encoder, wherein the transmit elements are arranged in the sensor array such that only one of the plurality of transmit elements is closest to a surface of a part under test at any point in time, and wherein the processing circuitry is configured to activate, based on the signal from the shaft encoder, only that transmit element closest to the surface of the part under test.

12. The drum sensor of claim 11, wherein each of the plurality of transmit elements and receive elements comprises an eddy current coil.

13. The drum sensor of claim 11, wherein the outer portion is an acoustic material.

14. The drum sensor of claim 11, wherein each of the plurality of transmit elements comprises an ultrasonic transducer configured to output an acoustic signal upon activation and wherein each of the plurality of receive elements comprises an ultrasonic transducer configured to receive a return acoustic signal reflected by a part under test.

15. A method for performing structural integrity testing, comprising the steps of:
receiving an input signal from a shaft encoder coupled to a drum sensor, the drum sensor having a shaft, a barrel-shaped inner portion mounted on the shaft, a sensor array positioned on an outer surface of the barrel-shaped inner portion and having a plurality of transmit elements and a plurality of receive elements, the transmit elements separate from the receive elements, the transmit elements positioned perpendicular to the receive elements, the plurality of transmit elements arranged in parallel to each other around a circumference of the outer surface of the barrel-shaped inner portion and the plurality of receive elements arranged parallel to each other and perpendicular to the circumference of the outer surface of the barrel-shaped inner portion, each of the plurality of receive elements extending across the outer surface of the barrel-shaped inner portion, and an outer portion positioned over the sensor array, the input signal providing an indication of a position of the drum sensor with respect to a surface of a part under test;
identifying, based on the input signal from the shaft encoder, a transmit element among the plurality of transmit elements closest to the surface of the part under test;
activating only the identified transmit element;
receiving an input signal from each of a plurality of receive elements; and
calculating an output signal based on the received input signals from the plurality of receive elements.

* * * * *